(12) United States Patent
Qian

(10) Patent No.: US 7,488,325 B2
(45) Date of Patent: Feb. 10, 2009

(54) FEMORAL NECK RESECTION GUIDE

(76) Inventor: Benwen Qian, 4501 Fu-Qieng-Pieng Road, Qieng-Pu District, Qieng-Pu, Shanghai (CN) 201700

( * ) Notice: Subject to any disclaimer, the term of this patent is extended or adjusted under 35 U.S.C. 154(b) by 146 days.

(21) Appl. No.: 10/499,641

(22) PCT Filed: Dec. 30, 2002

(86) PCT No.: PCT/CN02/00926

§ 371 (c)(1),
(2), (4) Date: Jun. 28, 2004

(87) PCT Pub. No.: WO03/055400

PCT Pub. Date: Jul. 10, 2003

(65) Prior Publication Data

US 2005/0080426 A1  Apr. 14, 2005

(30) Foreign Application Priority Data

Dec. 29, 2001  (CN)  ............................. 01 2 77173

(51) Int. Cl.
*A61B 17/56* (2006.01)
(52) U.S. Cl. ..................... 606/96; 408/115 R

(58) Field of Classification Search ............ 606/79, 606/80, 86, 87, 89, 96, 104, 53–59, 88, 97, 606/98; 623/22.12; 408/115 R, 103, 241 G; 30/296.1
See application file for complete search history.

(56) References Cited

U.S. PATENT DOCUMENTS

| 2,416,228 | A | * | 2/1947 | Sheppard .................... 408/105 |
| 3,945,377 | A | * | 3/1976 | Kronner ...................... 606/96 |
| 4,896,663 | A | * | 1/1990 | Vandewalls .................. 606/79 |
| 5,376,126 | A | | 12/1994 | Lin |
| 5,735,647 | A | * | 4/1998 | Woodings et al. ........... 408/103 |
| 6,267,762 | B1 | * | 7/2001 | Millard et al. ................ 606/54 |
| 6,322,564 | B1 | * | 11/2001 | Surma ......................... 606/79 |

* cited by examiner

*Primary Examiner*—Eduardo C Robert
*Assistant Examiner*—Richard Shaffer
(74) *Attorney, Agent, or Firm*—Bacon & Thomas, PLLC

(57) ABSTRACT

The present invention relates to an apparatus for fitting a protecting femoral neck device. The said apparatus includes a clamping base. A fixation element whose circumference size can be adjusted according to the size of the femoral neck in mounted on an end of the said clamping base and a locating element is mounted on the other end of the said clamping base. An element for shaping the bone can be fixed on the said locating element.

4 Claims, 4 Drawing Sheets

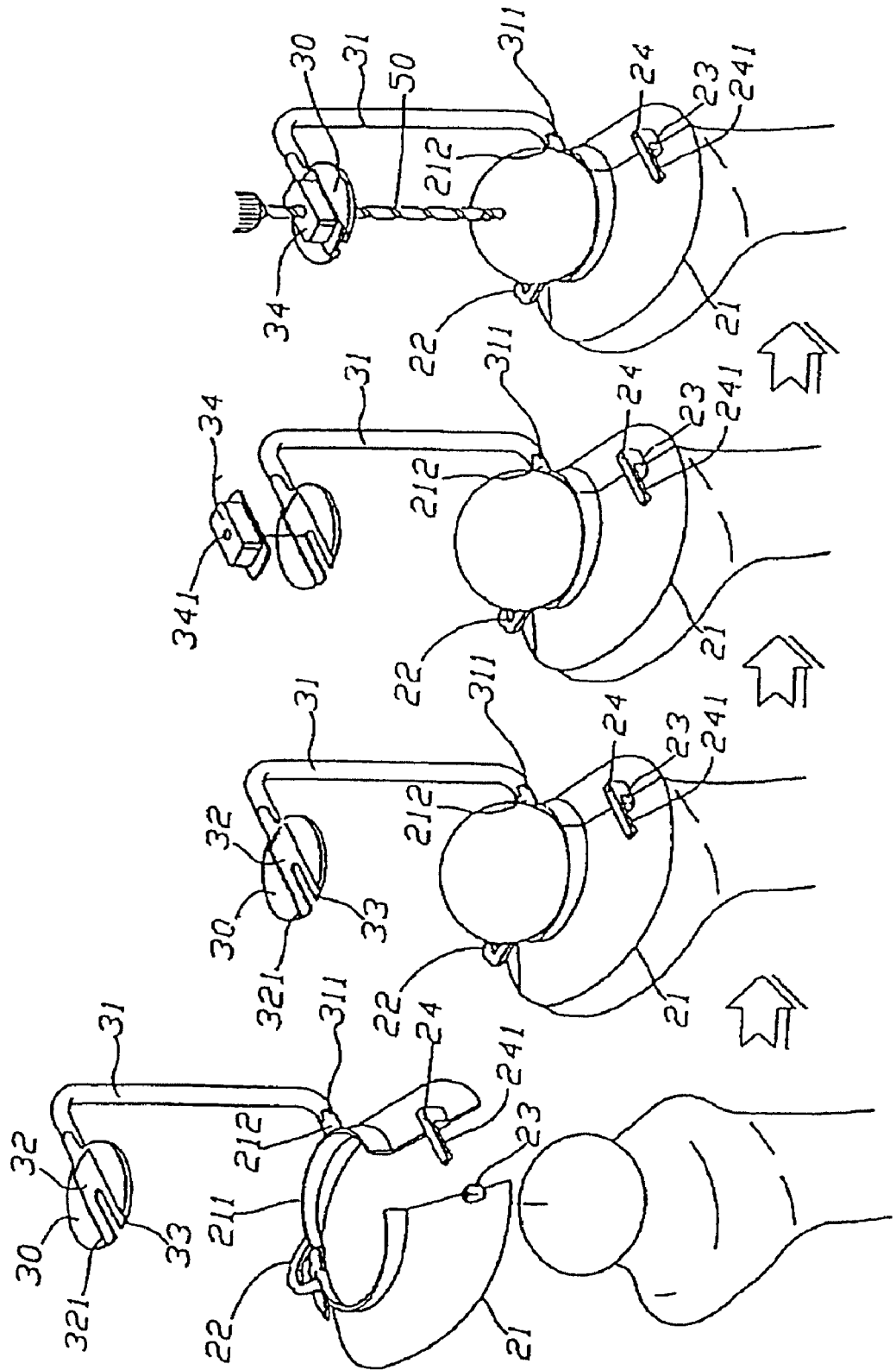

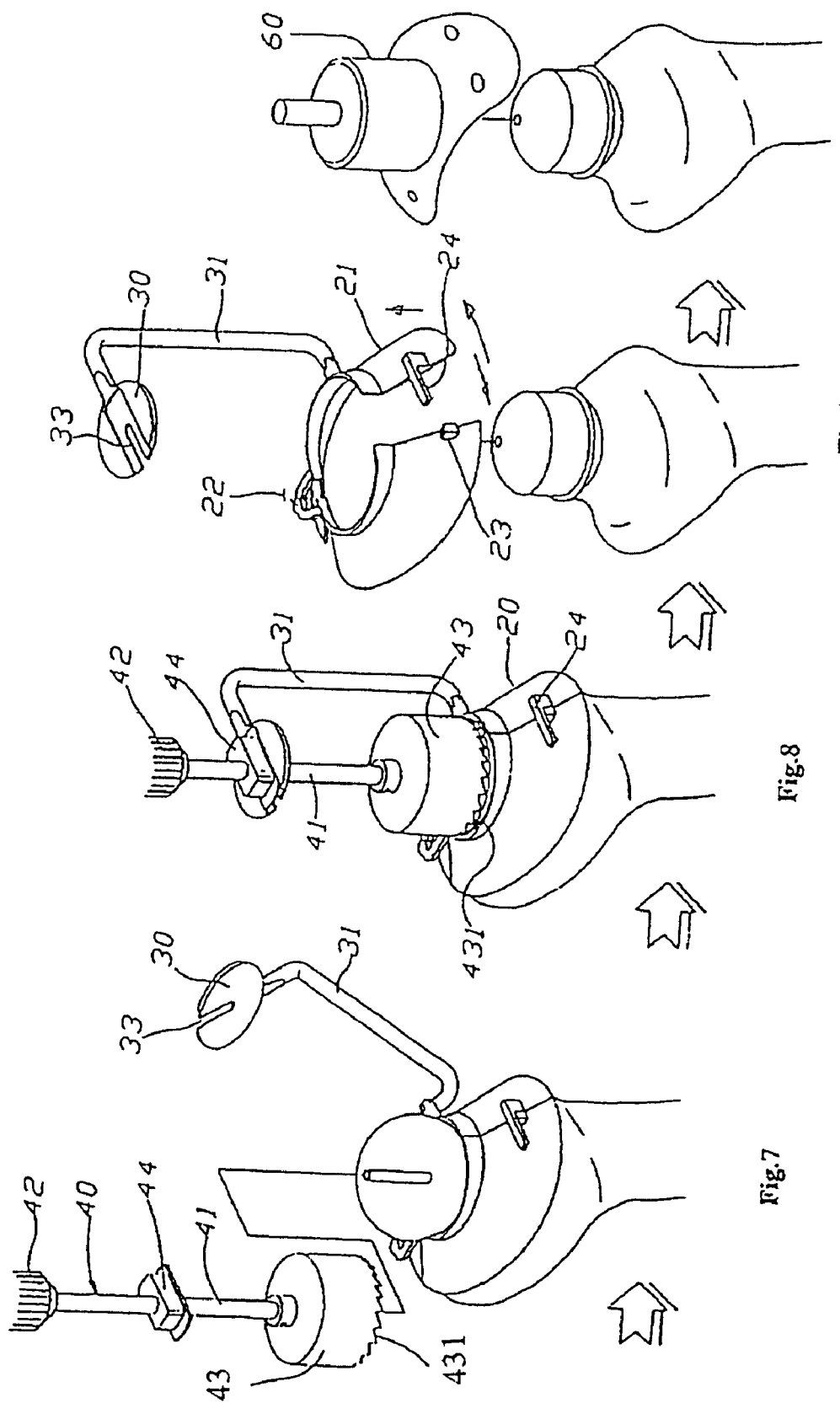

FEMORAL NECK RESECTION GUIDE

BACKGROUND OF THE INVENTION

1. Field of the Invention

The present invention relates to a medical apparatus for fitting a protecting femoral neck device, more particularly to an apparatus for easily fitting a protecting femoral neck device onto an injured femoral neck that can shorten the time of the surgical operation and reduce the patient's pain.

2. Description of the Related Art

In general, the method for connecting a femoral neck is nothing more than covering the femoral neck with a sheet steel and fixing into the femur. Since poor structure and design for such connection are common, therefore the foregoing method has the drawbacks that the fixation and coverage are not stable, and the newly grown blood vessels and callous formations cannot effectively cover the whole steel material. The sheet steel cannot be coupled with the femur fully as a whole for the protection, and thus limits the endurance of the femur and the covered steel material for bearing forces and usually results in an easy separation. Such method has a significant deficiency in its application and increases the pain of the patient. The foregoing drawbacks have been bothering medical staffs and the patients for long.

To overcome the foregoing drawbacks, a protecting femoral neck device is invented. The protecting femoral neck device is a hollow sleeve which comprises a screw passing through the sleeve for protecting the femoral neck from being injured again. However, before the prosthetic device can be used, the injured femur must be cut into the shape that precisely fits the connection of the sleeve onto the cut femur, so that the flange of the sleeve can attach closely onto the surface of the femur, and then a screw is secured to the bone connected with the femoral neck. The current common installation method adopts an operating knife or a reamer for the surgical operation and bases on the surgeon's experience to slowly cut the femoral neck into the required shape. Such arrangement not just takes a long time for the surgical operation, but also has difficulty for precisely cutting the femur into the required size or may even cause pain to the patient during the surgical operation.

SUMMARY OF THE INVENTION

Therefore it is the primary objective of the present invention to provide a technical solution for the foregoing problems as well as an apparatus for easily fitting a protecting femoral neck device onto an injured femoral neck that can shorten the time of the surgical operation and reduce the patient's pain.

The technical measures taken by the present invention to solve the foregoing problems by providing an apparatus for fitting the protecting femoral neck device that comprises: a clamping base, and the clamping base has a fixation element thereon, and the fixation element is comprised of two symmetrical semicircular rings. The semicircular rings are pivotally coupled with each other at one end and selectively opened and closed at the other end, and the clamping base further comprises a movable locating element being disposed at position corresponding to the fixation element and keeping a predetermined distance from the fixation element, and the locating element comprises an open groove and a broach being sheathed onto the clamping base and having a support rod disposed on the broach, and the support rod has a locating member and is coupled to a sleeve, and the sleeve has a serration disposed at the periphery of an opening of the sleeve. It is obvious that the following beneficial results will be obtained when the aforementioned solution is adopted. The structure of this invention is feasible, and the idea is great. The fixation element can be adjusted according to the size of the femoral neck for its application, so that the fixation element can be clamped and fixed onto the femoral neck. After a boring head is connected to the fixation element at a specific position of a boring hole on the femur, the broach passes into the fixation element and connects to a portion of the periphery of the femoral neck. Therefore, the femur can be grinded into the required shape, and a surgeon can easily fit the protecting femoral neck device onto the femoral neck. The present invention is simple-to-use and easy-to-install and thus worthy for its promotion.

To make it easier for our examiner to understand the objective of the invention, its structure, innovative features, and performance, we use a preferred embodiment together with the attached drawings for the detailed description of the invention.

BRIEF DESCRIPTION OF THE DRAWINGS

FIG. 3 is a perspective view of the clamping base being coupled to the femoral neck according to the present invention.

FIG. 4 is a perspective view of the disassembled structure of the clamping base being coupled to the femoral neck according to the present invention.

FIG. 5 is a perspective view of the clamping base being coupled to the femoral neck for its use according to the present invention.

FIG. 6 is a perspective view of the clamping base being coupled to the femoral neck for boring according to the present invention.

FIG. 7 is a perspective view of the broach as depicted in FIG. 1 being coupled to the clamping base according to the present invention.

FIG. 8 is a perspective view of the broach when it is boring according to the present invention.

FIG. 9 is a perspective view of the broach and the clamping base being removed from the femoral neck according to the present invention.

FIG. 10 is a perspective view of the apparatus for easily fitting a protecting femoral neck device being coupled to the femoral neck for boring according to the present invention.

DETAILED DESCRIPTION OF THE PREFERRED EMBODIMENTS

Figure 1:
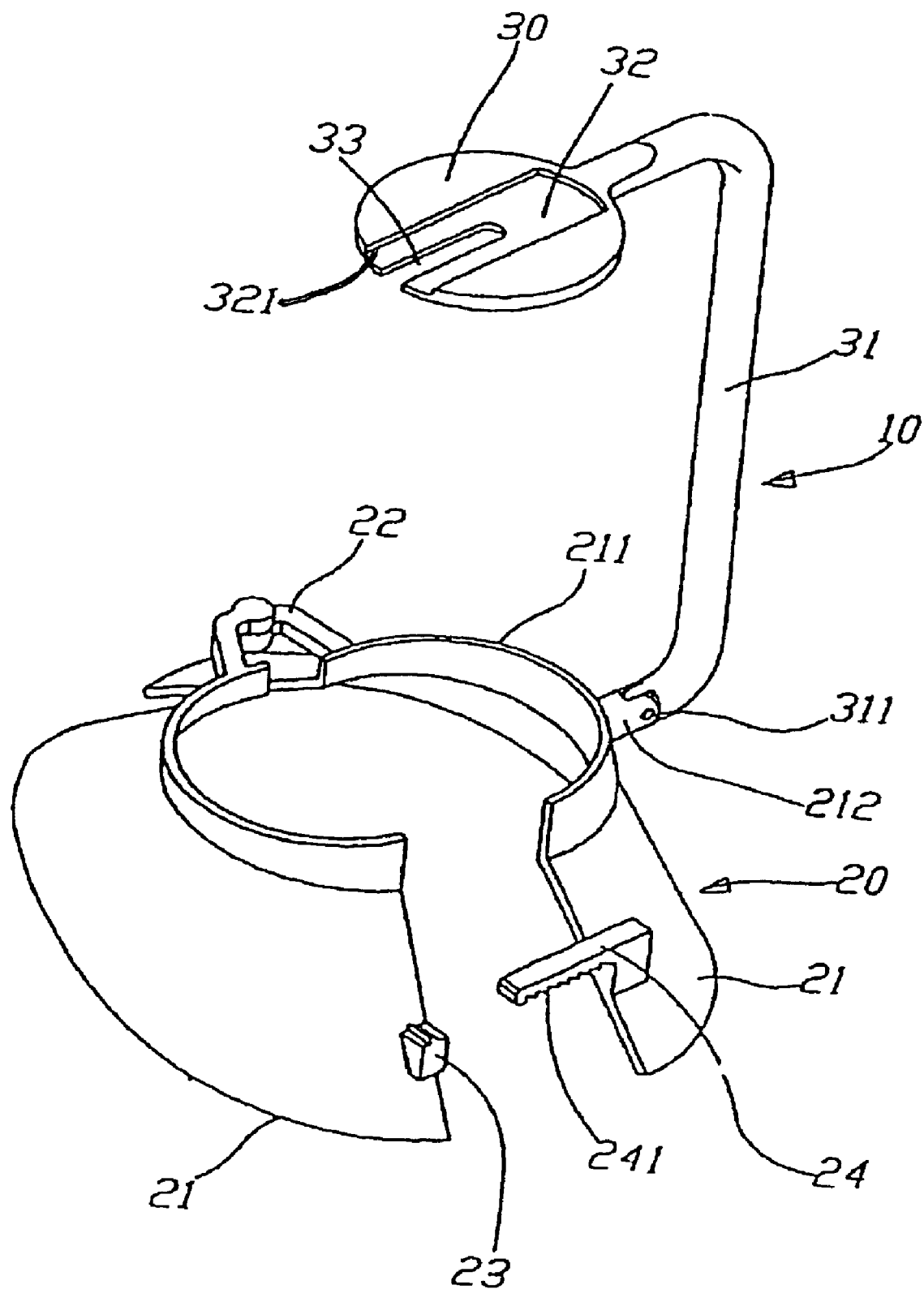
FIG. 1 is a perspective view of the disassembled apparatus for easily fitting a protecting femoral neck device according to the present invention.
Figure 2:
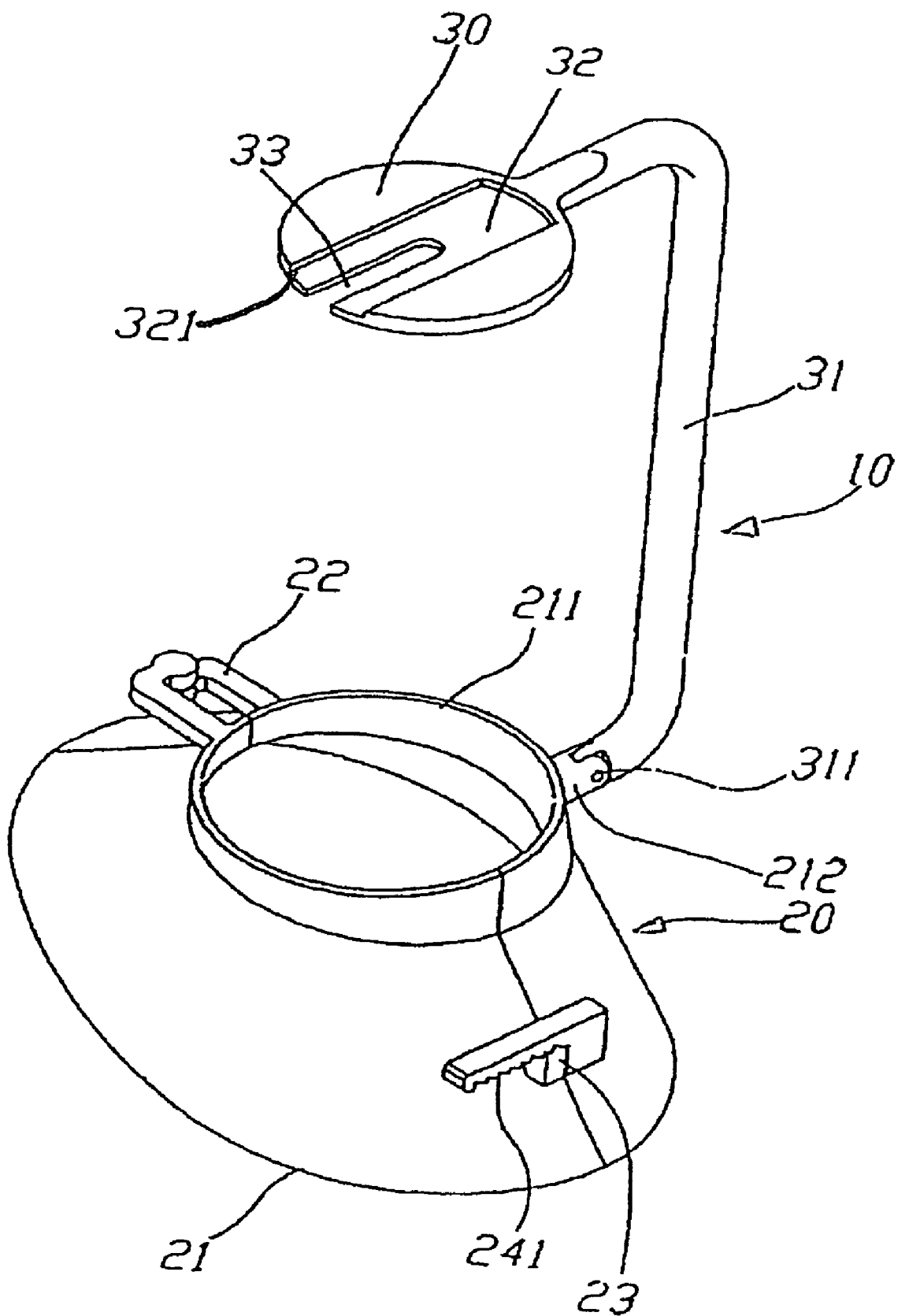
FIG. 2 is a perspective view of the apparatus for easily fitting a protecting femoral neck device according to the present invention.

Please refer to FIGS. 1 and 2 for an apparatus for fitting a protecting femoral neck device according to the present invention. The apparatus comprises a clamping base 10, and the clamping base 10 has a fixation element 20, and the fixation element 20 is in a tapered shape and comprised of two symmetrical semicircular rings 21, and the semicircular rings 21 has an upwardly extending flange 211 disposed at an inwardly contracted end, and a pivotal member 22 for movably coupled the semicircular rings 21 is disposed at one end of the flanges 211, and thus the connection of the semicircular rings 21 by the pivotal member 22 can couple the semicircular rings as well as providing the opening and closing functions. Further, an embedding body 23 and a corresponding serrated bar 24 are disposed on the surface of an edge at the other end of the semicircular rings 21; wherein the serrated bar 24 is comprised of a plurality of equidistant serrations 241, so that the embedding body 23 can be embedded into one of the serrations 241 of the serrated bar 24 according to the size of the femoral neck when the apparatus is in use. Then, the fixation element 2 can be mounted closely to the femoral neck and cannot be rotated freely as shown in FIG. 4.

Further, one of the semicircular rings 21 of the fixation element 20 is pivotally coupled with a movable support rod 31 at a predetermined position, and the support rod 31 is coupled with a pivotal base 212 of the semicircular ring 21 by the insertion of an insert pin only, so that the support rod 31 can be inclined to an angle to be fixed onto the fixation element 20 and also moved outward. The support rod 31 has a locating element 30 on the other end corresponding to the fixation element 20, and the locating element 30 is a cup structure for this embodiment. The locating element 30 comprises an indented plane 32, an open groove 33 disposed on the indented plane 32, an embedded groove 321 disposed on the periphery of the indented plane 32, a locating member 34 disposed on plane 32 and attached onto the embedded groove 321, and a through hole disposed on the locating member 34 corresponding to the open groove 33 as shown in FIG. 5.

Please refer to FIGS. 7, 8 and 9. The clamping base comprises a broach 40, a support rod 41 disposed on the broach 40, a locating member 44 disposed on the support rod 41, a rotary base 42 coupled to an end of the support rod 41, a sleeve 43 disposed on the other end of the support rod 41, and a serration 431 disposed at the periphery of an open end of the sleeve 43.

Please refer to FIGS. 3 to 10 for using. The connected ends of the semicircular rings 21 of the fixation element 20 are opened first as shown in FIG. 3, and the fixation element 2 is sheathed onto the femoral neck, and the embedded body 23 on one semicircular ring 21 is latched into the serration 241 of the serrated bar 24 of another semicircular ring 21 according to the size of the injured femur, so that the fixation element 20 can be secured onto the femur as shown in FIG. 4, and then the locating member 34 is embedded on the locating element 30 as shown in FIG. 5. A boring head 50 passes through a through hole 341 and implanted deeply into the surface of the femur, so that the boring head 50 can rotate at a fixed position under the limitation of the through hole 341 and drill a hole at the center of the femur to a predetermined depth as shown in FIG. 6.

Later, the boring head 50 is withdrawn from the femur to move the locating element 30 outward as shown in FIG. 7 and the sleeve 43 of the broach 41 connects to the periphery of the femoral neck, and the locating element 30 returns to its original position to move the locating member 44 on the support rod 42 to a position corresponding to the locating element 30. In the meantime, the locating member 44 embedded in the plane 32 of the locating element 30, so that the broach 40 can used the center of the locating element 30 for carrying out the grinding and rotate the sleeve 43 under the limitation of the open groove 33 of the locating element 30. As a result, the serrations 431 at the sleeve 43 disposed on the periphery of femur cut and grind the femur into a required shape as shown in FIG. 8. Then, the clamping base 10 and the broach 40 are removed from the femur as shown in FIG. 9 to allow the surgeon to fit the protecting femoral neck device 60 onto the femur as shown in FIG. 10. The present invention has the simple-to-use and easy-to-install functions.

In summation of the description above, the present invention overcomes the shortcomings of the prior-art and enhances the performance than the conventional structure and further complies with the patent application requirements and is submitted to the Patent Office for review and granting of the commensurate patent rights.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements.

What is claimed is:

1. An apparatus for fitting a protecting femoral neck device, comprising:
   a fixation element having two symmetrical semicircular rings, each having a tapered shape and an upwardly extending flange at the tapered end thereof;
   a pivotal member disposed at a first end of the respective flange of each semicircular ring, and pivotally connecting said semicircular rings such that the semicircular rings can:
     a) pivot away from each other to define an opening opposite to the pivotal member; and
     b) pivot towards each other to form a closed ring;
   a pivotal base directly connected to the flange of one of the semicircular rings;
   a movable support rod connected at a first end thereof to the pivotal base by an insert pin, wherein the movable support rod is pivotally coupled to one of the semicircular rings by way of the pivotal base and insert pin such that the movable support rod can pivot towards and away from the semicircular ring to which it is coupled; and
   a movable locating element positioned at an end of the movable support rod opposite the first end, and having:
     an indented plane;
     an open groove disposed on the indented plane and defining an opening through the indented plane and further open at an edge of the indented plane; and
     an embedded groove disposed around a periphery of the indented plane and also open at the edge of the indented plane.

2. The apparatus for fitting a protecting femoral neck device of claim 1, further comprising a locating member configured to be disposed on the indented plane and fittingly engaged with the embedded groove, wherein the locating member includes a vertical through hole which aligns with the open groove when the locating member is fittingly engaged with the embedded groove.

3. The apparatus for fitting a protecting femoral neck device of claim 1, further comprising a coring device, the coring device having:
   a second support rod;
   a locating member through which the second support rod passes, and which is configured to fittingly engage with the embedded groove such that the support rod passing through the locating member aligns with the open groove; and
   a sleeve attached to one end of the support rod, and having serrations disposed at a periphery of an open end of the sleeve.

4. The apparatus for fitting a protecting femoral neck device of claim 1, further comprising an embedding body located at a second end of one semicircular ring spaced from the pivotal member and a serrated bar located at a second end of the other semicircular ring spaced from the pivotal member, wherein the serrated bar comprises a plurality of equidistant serrations such that when the semicircular rings are pivoted towards each other, the embedding body is embedded into one of the serrations.

* * * * *